United States Patent
Kuo et al.

(10) Patent No.: US 11,965,852 B2
(45) Date of Patent: Apr. 23, 2024

(54) MICROELECTROMECHANICAL SENSOR AND SENSING MODULE THEREOF

(71) Applicant: INDUSTRIAL TECHNOLOGY RESEARCH INSTITUTE, Hsinchu (TW)

(72) Inventors: Pei-Chi Kuo, Tainan (TW); Bor-Shiun Lee, New Taipei (TW); Ming-Fa Chen, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 101 days.

(21) Appl. No.: 17/719,342

(22) Filed: Apr. 12, 2022

(65) Prior Publication Data
US 2023/0213466 A1 Jul. 6, 2023

(30) Foreign Application Priority Data
Jan. 5, 2022 (TW) .................................. 111100333

(51) Int. Cl.
*G01N 27/12* (2006.01)
*G01N 33/00* (2006.01)

(52) U.S. Cl.
CPC ....... *G01N 27/128* (2013.01); *G01N 33/0062* (2013.01)

(58) Field of Classification Search
CPC .......................... G01N 33/0062; G01N 27/128
USPC ......................................................... 73/31.06
See application file for complete search history.

(56) References Cited

U.S. PATENT DOCUMENTS

| | | | |
|---|---|---|---|
| 6,326,229 B1 * | 12/2001 | Mastromatteo | G01N 27/12 257/253 |
| 7,892,794 B2 * | 2/2011 | Jensen | C12Q 1/04 435/91.1 |
| 7,963,147 B2 | 6/2011 | Jun et al. | |
| 8,449,177 B2 * | 5/2013 | Kvisteroy | G01L 21/00 374/185 |
| 9,658,179 B2 | 5/2017 | Rajaraman et al. | |
| 10,527,571 B2 * | 1/2020 | Udrea | H05B 3/0047 |
| 10,843,919 B2 * | 11/2020 | Chen | B81B 7/009 |
| 11,041,838 B2 * | 6/2021 | Rogers | G01N 25/48 |

(Continued)

FOREIGN PATENT DOCUMENTS

| | | |
|---|---|---|
| CN | 103675048 B | 2/2016 |
| CN | 205506741 U | 8/2016 |

(Continued)

OTHER PUBLICATIONS

Translation of KR-100937593-B1 (Year: 2010).*
TW Office Action dated Apr. 17, 2023 as received in Application No. 111100333.

*Primary Examiner* — Nathaniel T Woodward
(74) *Attorney, Agent, or Firm* — Maschoff Brennan

(57) ABSTRACT

A microelectromechanical sensor includes a base, a heater provided on the base, and a sensing electrode including a sensing portion. The heater includes a heating portion. The heater and the sensing electrode are provided at different layers in a stacking direction, and the sensing electrode is electrically insulated from the heater. On a reference plane in the stacking direction, a projection of the sensing portion of the sensing electrode is entirely covered by a projection of the heating portion of the heater.

19 Claims, 7 Drawing Sheets

(56) References Cited

U.S. PATENT DOCUMENTS

| | | | |
|---|---|---|---|
| 2008/0134753 A1* | 6/2008 | Jun | G01N 27/128 73/23.2 |
| 2009/0151429 A1* | 6/2009 | Jun | G01N 27/128 73/31.06 |
| 2010/0147070 A1* | 6/2010 | Jun | G01N 27/121 216/13 |
| 2010/0180668 A1* | 7/2010 | Kruse | G01N 15/0656 73/28.01 |
| 2010/0264900 A1* | 10/2010 | Blackburn | G01N 27/4071 73/31.06 |
| 2012/0217550 A1* | 8/2012 | Usagawa | G01N 27/4141 257/253 |
| 2014/0210036 A1* | 7/2014 | Sunier | G01F 1/6845 438/49 |
| 2015/0285772 A1* | 10/2015 | Park | G01N 27/123 73/31.05 |
| 2017/0066646 A1* | 3/2017 | Cheng | B81C 1/00301 |
| 2017/0131252 A1* | 5/2017 | Ahn | H05B 3/03 |
| 2017/0168009 A1 | 6/2017 | Liao et al. | |
| 2018/0313800 A1* | 11/2018 | Rogers | G01N 33/0013 |
| 2018/0372674 A1 | 12/2018 | Diehl et al. | |
| 2019/0383721 A1* | 12/2019 | Eom | F01N 13/008 |
| 2020/0064292 A1 | 2/2020 | Chang et al. | |
| 2021/0198101 A1 | 7/2021 | Lee et al. | |
| 2021/0262967 A1 | 8/2021 | Tatara et al. | |

FOREIGN PATENT DOCUMENTS

| | | | | |
|---|---|---|---|---|
| CN | 207423635 U | | 5/2018 | |
| CN | 110651179 A | | 1/2020 | |
| JP | 2007132762 A | | 5/2007 | |
| KR | 100937593 B1 | * | 1/2010 | G01N 27/4067 |
| TW | 201538970 A | | 10/2015 | |
| TW | 201732281 A | | 9/2017 | |
| TW | I623743 B | | 5/2018 | |
| TW | I672487 B | | 9/2019 | |
| TW | I705245 B | | 9/2020 | |
| TW | I717178 B | | 1/2021 | |
| WO | 2019234998 A1 | | 12/2019 | |

* cited by examiner

MICROELECTROMECHANICAL SENSOR AND SENSING MODULE THEREOF

CROSS-REFERENCE TO RELATED APPLICATIONS

This non-provisional application claims priority under 35 U.S.C. § 119(a) on Patent Application No(s). 111100333 filed in Taiwan R.O.C on Jan. 5, 2022, the entire contents of which are hereby incorporated by reference.

BACKGROUND

1. Technical Field

This present disclosure relates to a microelectromechanical sensor and a sensing module thereof.

2. Related Art

For public safety and public health, efficient detection and monitoring of industrial toxic gases, flammable gases, and explosive gases, hazardous gases in chemical laboratories, and harmful gases associated with diseases are greatly important. Accordingly, the development of gas sensors with high sensitivity, high selectivity, fast response rate, and long service life is one of the subjects in this technical field.

Some semiconductor materials and metal oxides have been discovered and applied in the microelectromechanical gas sensors due to their excellent gas sensitive properties. In general, to obtain gas sensitive properties for actual requirements, the semiconductor materials and metal oxides should be heated at a specific temperature, such that the gas sensors are usually equipped with elements for heating to keep an appropriate temperature for the operation of the gas sensors.

SUMMARY

According to one embodiment of the present disclosure, a microelectromechanical sensor includes a base, a heater provided on the base, and a sensing electrode including a sensing portion. The heater includes a heating portion. The heater and the sensing electrode are provided at different layers in a stacking direction, and the sensing electrode is electrically insulated from the heater. On a reference plane in the stacking direction, a projection of the sensing portion of the sensing electrode is entirely covered by a projection of the heating portion of the heater.

According to another embodiment of the present disclosure, a sensing module for gas concentration monitoring includes a heater including a heating portion, and a sensing electrode including a sensing portion. The heater and the sensing electrode are provided at different layers in a stacking direction, and the sensing electrode is electrically insulated from the heater. On a reference plane in the stacking direction, a projection of the sensing portion of the sensing electrode is entirely covered by a projection of the heating portion of the heater.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present disclosure. The following embodiments further illustrate various aspects of the present disclosure, but are not meant to limit the scope of the present disclosure.

Figure 1:
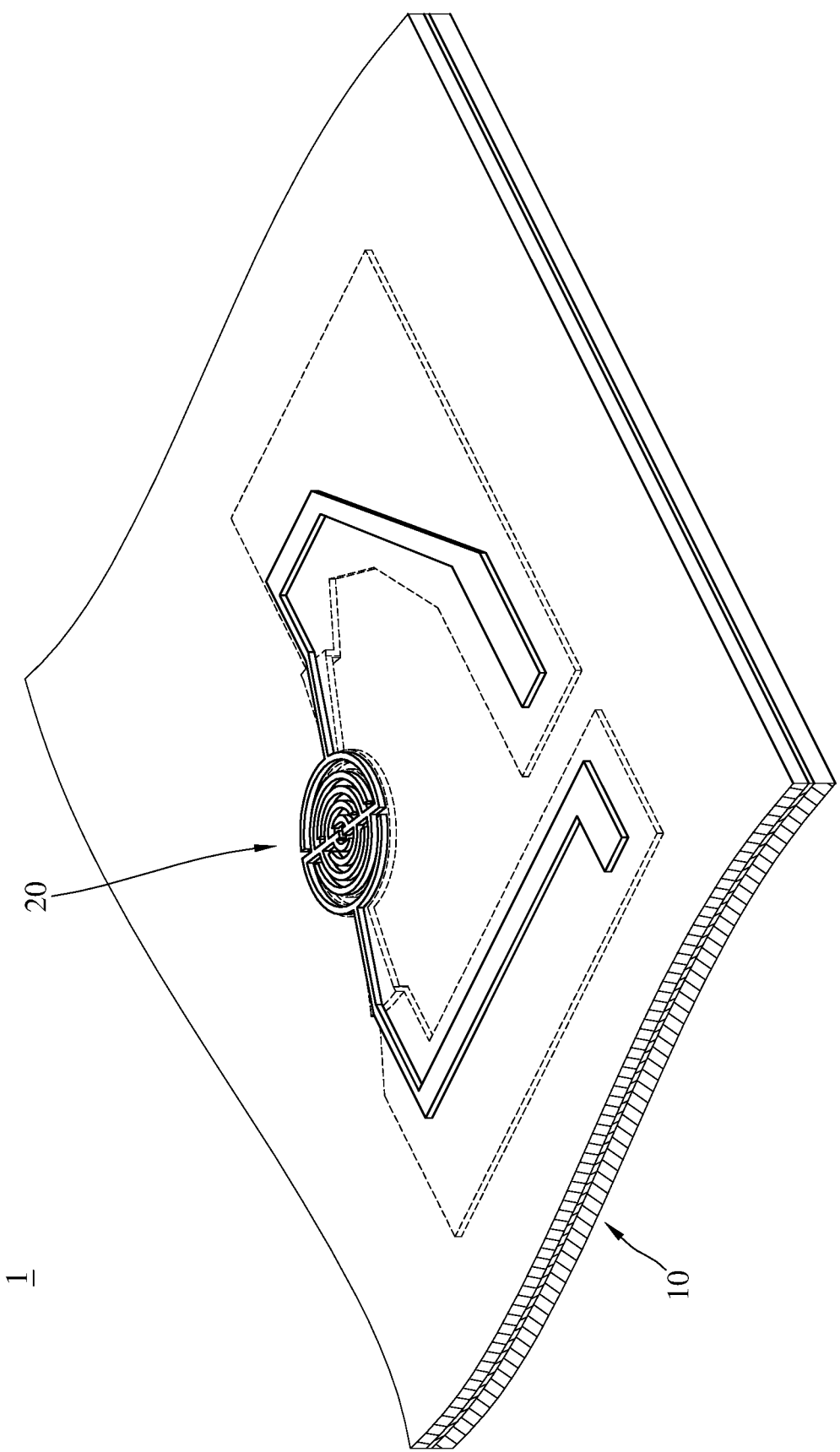
FIG. 1 is a perspective view of a microelectromechanical sensor according to one embodiment of the present disclosure.
Figure 2:
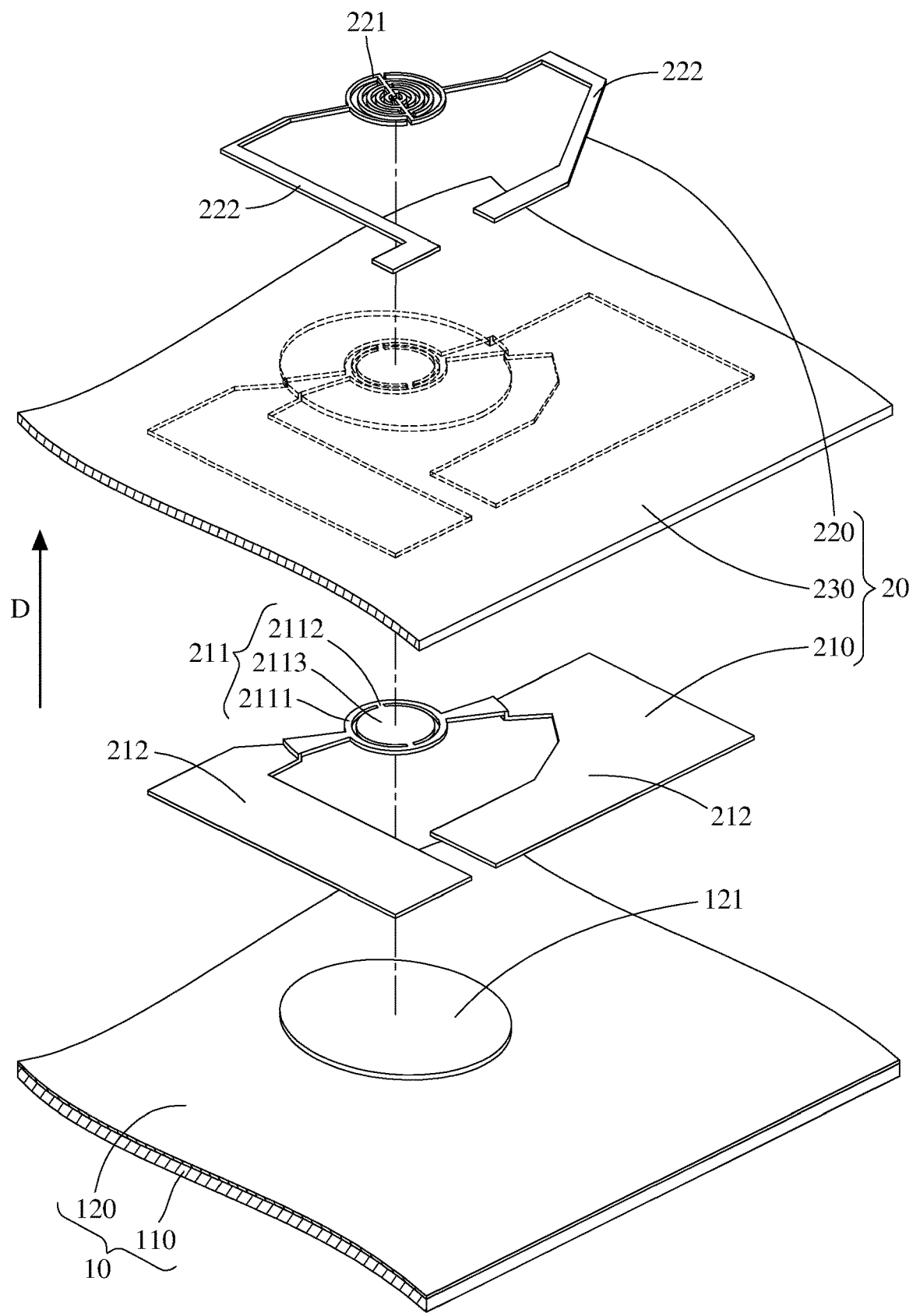
FIG. 2 is an exploded view of the microelectromechanical sensor in FIG. 1.
Figure 3:
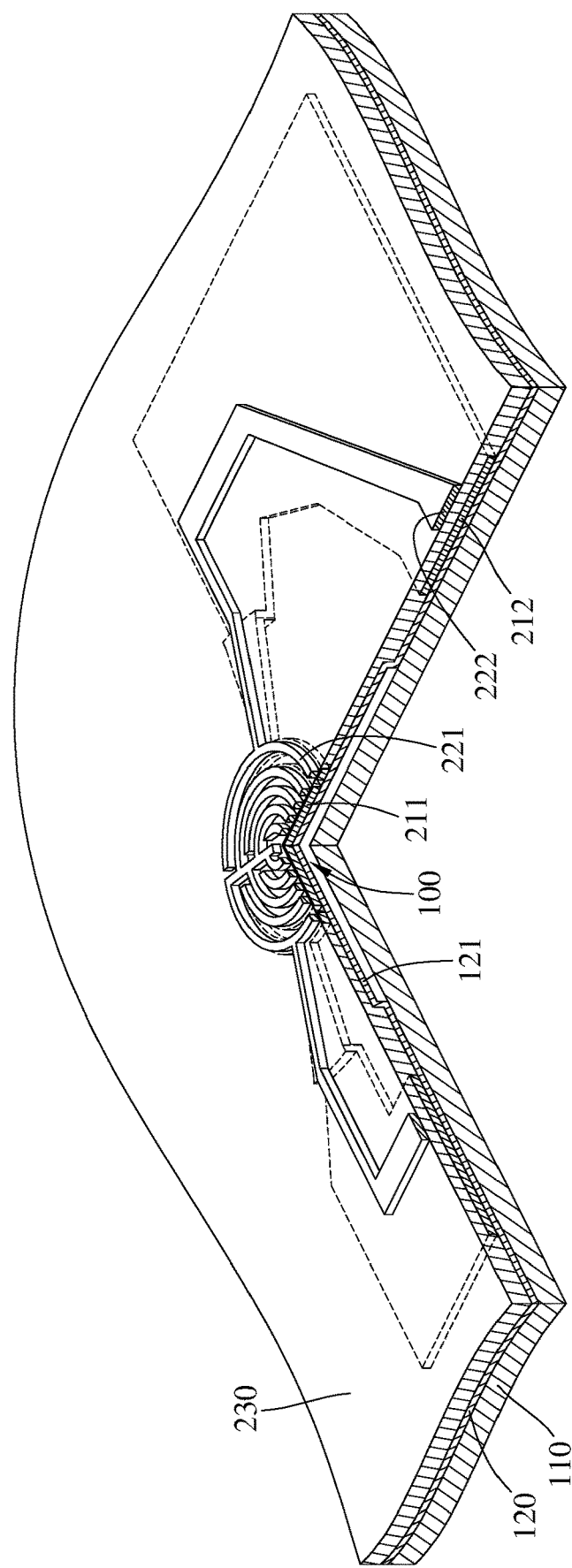
FIG. 3 is a cross-sectional view of the microelectromechanical sensor in FIG. 1.

Please refer to FIG. 1 through FIG. 3. FIG. 1 is a perspective view of a microelectromechanical sensor according to one embodiment of the present disclosure, FIG. 2 is an exploded view of the microelectromechanical sensor in FIG. 1, and FIG. 3 is a cross-sectional view of the microelectromechanical sensor in FIG. 1. In this embodiment, a microelectromechanical sensor 1 includes a base 10 and a sensing module 20.

The base 10 include a substrate 110, and a thermal insulating film 120 disposed on the substrate 110. The substrate 110 is, for example but not limited to, a silicon substrate or a glass substrate, and the thermal insulating film 120 is, for example but not limited to, a silicon oxide film. The thermal insulating film 120 includes a bump 121, and a thermal insulating cavity 100 is formed between the substrate 110 and the bump 121. More specifically, a sacrificial layer (not shown in the drawings) may be formed at a predetermined region on the surface of the substrate 110, then the thermal insulating film 120 may be formed above the substrate 110 and the sacrificial layer, and then the sacrificial layer may be removed, such that a space originally occupied by the sacrificial layer is taken as the thermal insulating cavity 100.

Figure 4:
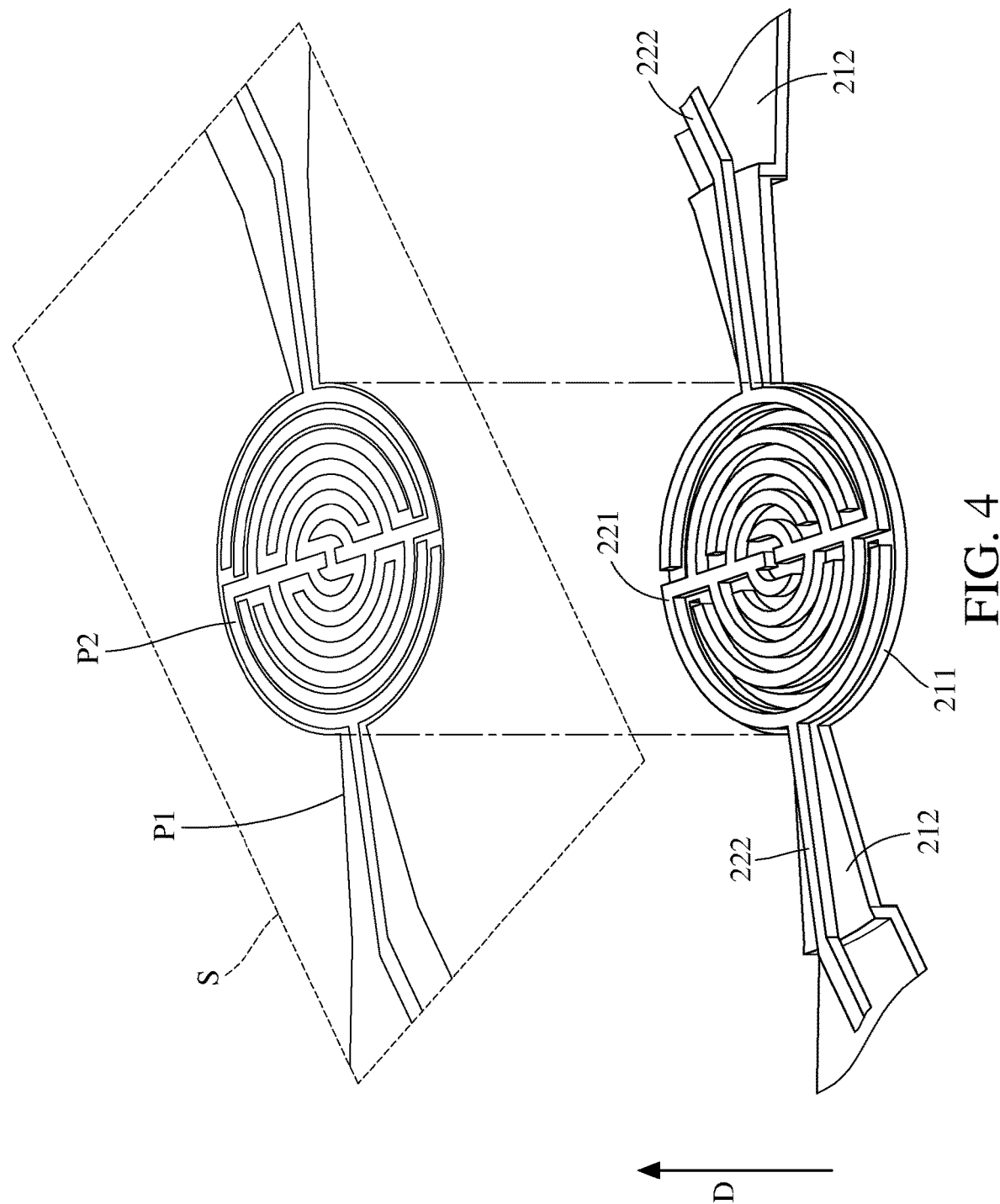
FIG. 4 is a perspective view of a sensing module in the microelectromechanical sensor of FIG. 1.
Figure 5:
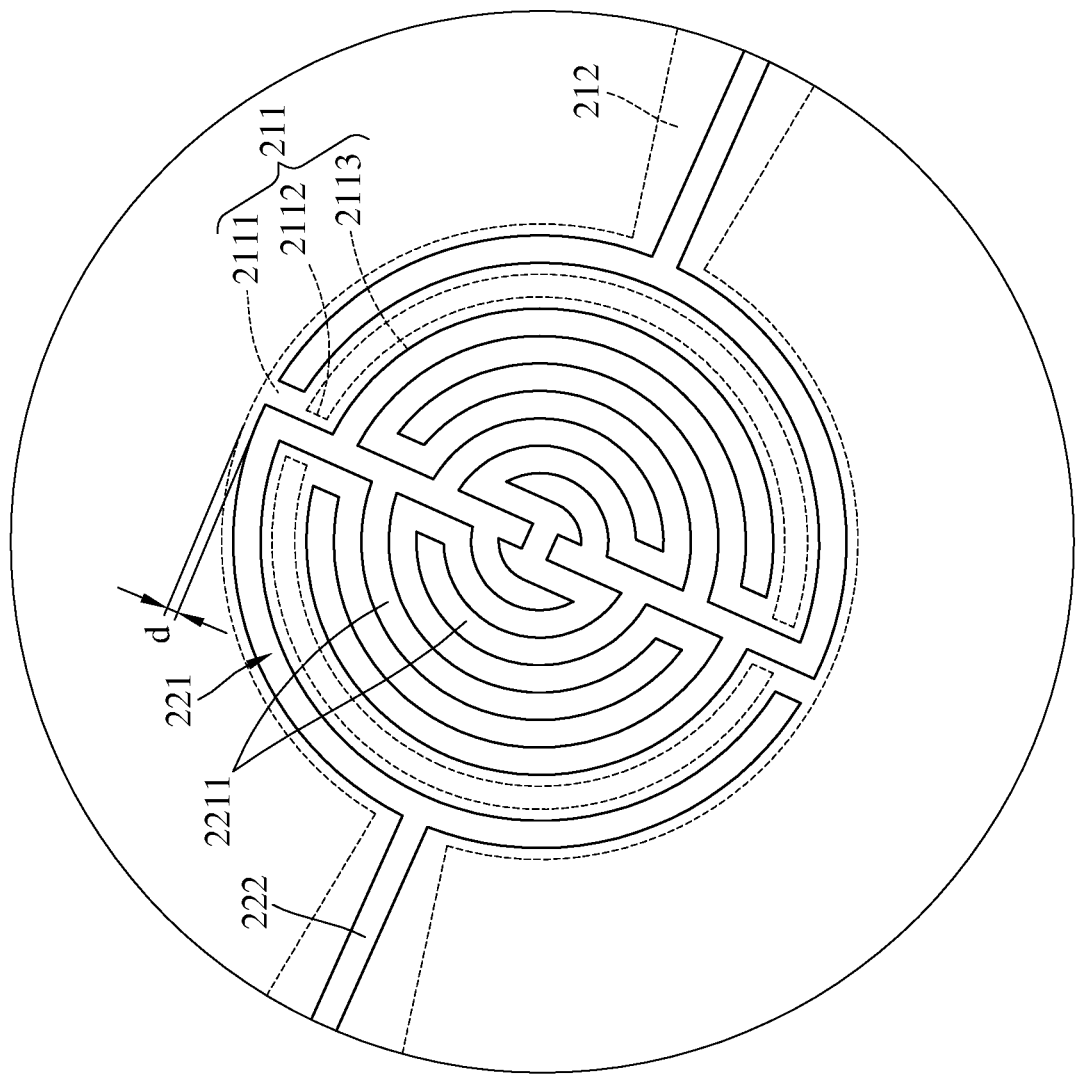
FIG. 5 is a top view of the sensing module in FIG. 4.

The sensing module 20 includes a heater 210, a sensing electrode 220 and an electrically insulating layer 230. Please refer to FIG. 4 and FIG. 5. FIG. 4 is a perspective view of a sensing module in the microelectromechanical sensor of FIG. 1, and FIG. 5 is a top view of the sensing module in FIG. 4. The heater 210 is, for example but not limited to, a resistive heater disposed on the base 10, and the heater 210 includes a heating portion 211. More specifically, the heater 210 includes a heating portion 211 and a heater arm 212 connected with each other, and the heating portion 211 is disposed to correspond with the thermal insulating cavity 100. The thermal insulating cavity 100 can reduce the amount of heat transferred to the substrate 110 to therefore prevent heat loss. The heating portion 211 of the heater 210 includes an outer frame section 2111, a connecting section 2112 and a disc section 2113. The outer frame section 2111 surrounds the connecting section 2112 and the disc section 2113, and the disc section 2113 is connected with the outer frame section 2111 through the connecting section 2112. The heating portion 211 may be electrically connected with an external power source (not shown in the drawings) through the heater arm 212. The external power source can supply electrical current to raise the temperature of the heater 210.

The sensing electrode 220 is, for example but not limited to, made of semiconductor material or metal oxide with good gas sensitive properties, and the heater 210 and the sensing electrode 220 are disposed at different layers in a stacking direction D. Specifically, along the stacking direction D, the sensing electrode 220 is disposed above the heater 210, and the sensing electrode 220 includes a sensing portion 221 and an electrode arm 222 connected with each other. The sensing portion 221 includes a comb-like structure consisting of one or more interdigitated electrodes 2211 corresponding with the heating portion 211. The sensing portion 221 is connected with an external reading circuit (not shown in the drawings) through the electrode arm 222 for generating electrical signals. In this embodiment, the sensing electrode 220 is provided above the heater 210, but the present disclosure is not limited thereto. In some other embodiments, the sensing electrode may be placed on the base, and followed by the heater provided on above the sensing electrode.

In this embodiment, the heating portion 211 is a portion of the heater 210 substantially increasing in temperature when the heater 210 is working. The sensing portion 221 is a portion of the sensing electrode 220 whose temperature is substantially influenced by the heater 210, or a portion thereof substantially having gas sensitive properties that meet requirements for gas concentration monitoring. Also, in some embodiments, the sensing portion 221 may preferably refer to every portion of the sensing electrode 220 which are substantially heated or have gas sensitive properties. For example, the sensing portion 221, as depicted in FIG. 5, refers to all interdigitated electrodes 2211 and the entire area of each interdigitated electrode 2211, rather than some of the interdigitated electrodes or partial area of each interdigitated electrode.

The electrically insulating layer 230 is, for example but not limited to, a non-conductive heat resistant plastic or oxide film disposed between the heater 210 and the sensing electrode 220 to electrically insulate the sensing electrode 220 from the heater 210. Specifically, the electrically insulating layer 230 is provided on the heater 210 to cover the sensing electrode 220, and therefore spatially separate the heater 210 from the sensing electrode 220. The sensing electrode 220 is provided on the electrically insulating layer 230.

As shown in FIG. 4, on a reference plane S in the stacking direction D, a projection of the sensing portion 221 of the sensing electrode 220 is entirely covered by a projection of the heating portion 211 of the heater 210. In detail, on the reference plane S, the projections of the heating portion 211 and the heater arm 212 cover the projections of the sensing portion 221 and the electrode arm 222, respectively; that is, the projection P2 of the sensing electrode 220 is entirely covered by the projection P1 of the heater 210, and the projection P1 may have a larger area than the projection P2. The ratio of the projection of the heater 210 (including a region overlapping the projection of the sensing electrode 220 and the other region which does not overlap the projection of the sensing electrode 220) to the projection of the sensing electrode 220 may be 2:1. This ratio may be 3:1 in some other embodiments, 4:1 in still some other embodiments. Further, as shown in FIG. 5, a distance (d) between the outermost edge of the outer frame section 2111 of the heating portion 211 and the outermost edge of an outermost interdigitated electrode 2211 of the sensing portion 221 may be from 0.1 micrometer (μm) to 0.3 μm to ensure high fabrication yield of the sensing module 20.

The temperature of the heating portion 211 of the heater 210 can be adjusted so as to maintain the temperature of the sensing portion 221 of the sensing electrode 220 at a suitable temperature for operation. When the sensing portion 221 adsorbs gas so as to generate a change in resistance value, the external reading circuit may response a change in voltage value or a change in current value, such that the type of gas can be recognized and its gas concentration can be monitored.

In this embodiment, the sensing electrode 220 is disposed above the heater 210, and the sensing portion 221 of the sensing electrode 220 extends to comply with the heating portion 211 of the heater 210; that is, the projections of the heating portion 211 and the sensing portion 221 and the overlap each other on the reference plane S, and the projection of the sensing portion 221 is entirely covered by the projection of the heating portion 211. This indicates that the sensing portion 221 of the sensing electrode 220 does not protrude laterally out of the heater 210, and does not cross a region between two of the outer frame section 2111, the connecting section 2112 and the disc section 2113 of the heating portion 211, thereby preventing a step difference in the topography of the sensing electrode 220 at a region where the heating portion 211 is formed. It is helpful to reduce breakage or incomplete etching of a fragile portion in the sensing electrode 220 due to the step difference in the topography thereof, thereby improving fabrication yield of the sensing electrode 220.

Moreover, since the sensing portion 221 does not cross any structure in the heating portion 211, all portions of the sensing portion 221 can be heated evenly by the heater 210, which helps to prevent deformation of the interdigitated electrode 2211 due to local thermal stress, thereby prolonging the service life of the microelectromechanical sensor 1.

Figure 6:
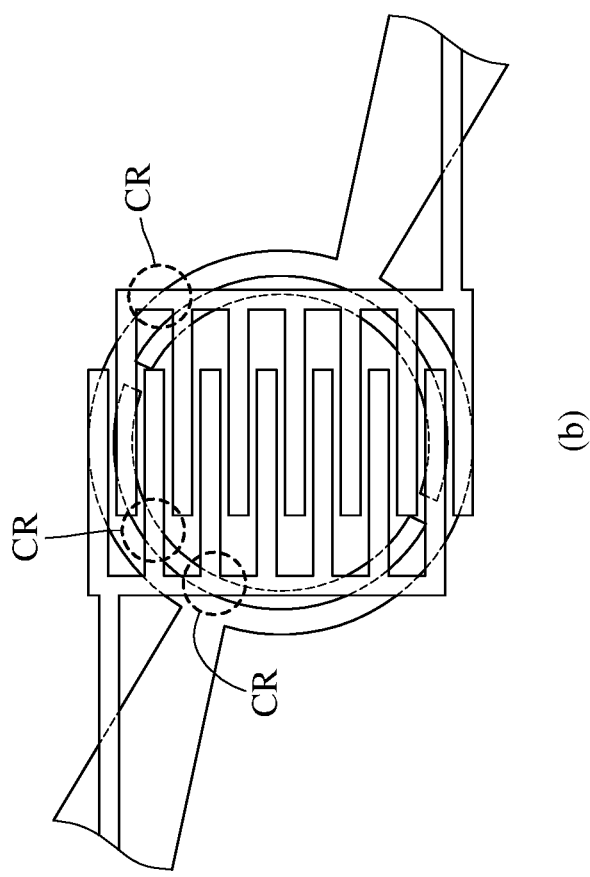
FIG. 6 is a schematic view showing the sensing module in FIG. 5 and a conventional sensing module.
Figure 6:
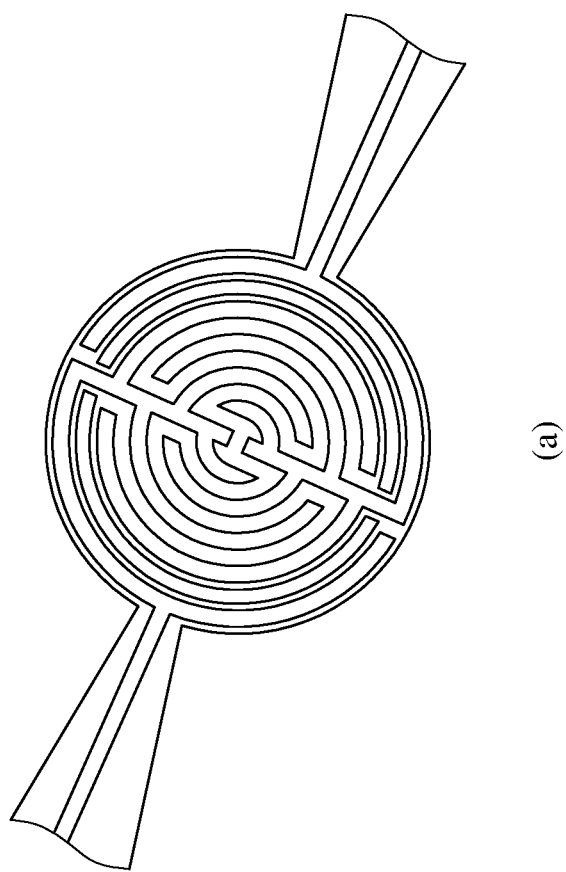

FIG. 6 is a schematic view showing the sensing module in FIG. 5 and a conventional sensing module. The sensing module 20 of FIG. 5, as depicted in FIG. 6(a), is taken to be in comparison with a sensing module in a conventional resistive-type gas sensor in which a sensing electrode extends to cross a heater, as depicted in FIG. 6(b). In a condition that the heaters work at the same temperature, it can be observed that the sensing electrode of the conventional sensing module suffers a higher temperature at a location CR where the sensing electrode crosses the heater, such that heat stress easily occurs at the location CR where the sensing electrode crosses the heater. In contrast, the sensing portion 221 of the sensing module 20 in this embodiment has a uniform temperature distribution, and therefore can reduce localized heat stress.

Furthermore, the heater 210 and the sensing electrode 220 in this embodiment are provided at different layers in the stacking direction D. For example, the heater 210 and the sensing electrode 220 are formed in different steps of the fabrication process, and the heater 210 and the sensing electrode 220 are not provided at the same level. Thus, a gap with proper size for accommodating the electrically insulating layer 230 is provided between any two of the outer frame section 2111, the connecting section 2112 and the disc section 2113 of the heating portion 211, and it is helpful to prevent short circuit due to that the heating portion 211 and the sensing portion 221 are overly close to each other.

Figure 7:
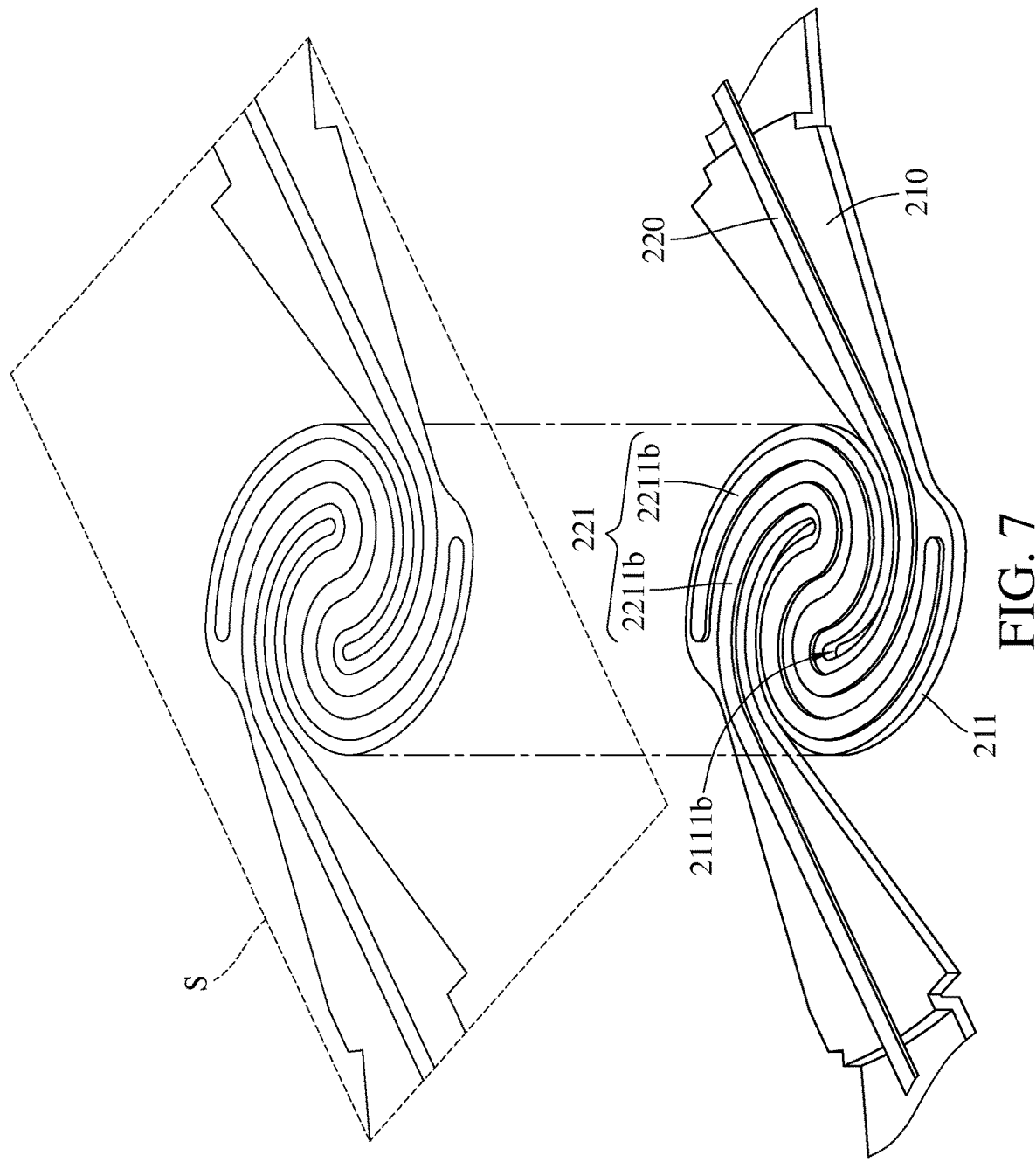
FIG. 7 is a perspective view of a sensing module according to another embodiment of the present disclosure.

FIG. 7 is a perspective view of a sensing module according to another embodiment of the present disclosure. In this embodiment, a sensing module 20b of a microelectromechanical sensor includes a heater 210 and a sensing electrode 220. The heating portion 211 of the heater 210 of the sensing module 20b includes a curved structure 2111b, and the curved structure 2111b is S-shaped in FIG. 7. The sensing portion 221 of the sensing electrode 220 includes a pair of working electrodes 2211b extending along the curved structure 2111b and arranged in parallel. Similar to the aforementioned embodiment(s), the heater 210 and the sensing electrode 220 are disposed at different layers in the stacking direction D. On the virtual reference plane S in the stacking direction D, the projection of the sensing portion 221 of the sensing electrode 220 is entirely covered by the projection of the heating portion 211 of the heater 210.

According to the present disclosure, the projection of the heating portion and the projection of the sensing portion overlap each other on the reference plane, and the projection of the sensing portion is entirely covered by the projection of the heating portion, which is helpful to prevent a step difference in the topography of the sensing electrode at a region where the heating portion is formed, so as to reduce breakage or incomplete etching of a fragile portion in the sensing electrode due to the step difference in the topography thereof, thereby improving fabrication yield of the sensing electrode. Also, every portion of the sensing portion can be heated evenly by the heater, which helps to prevent deformation of the sensing electrode due to local thermal stress, thereby prolonging the service life of the microelectromechanical sensor.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A microelectromechanical sensor, comprising:
a base, comprising a substrate and a thermal insulating film on a flat top surface of the substrate, wherein the thermal insulating film comprises a bump and a thermal insulating cavity, the bump protrudes upward from the thermal insulating film, such that the thermal insulating cavity is formed within a boundary defined by an inner profile of the bump and the flat top surface, the flat top surface of the substrate and a bottom surface of the thermal insulating film are aligned and in contact on same plane;
a heater provided on the base, and the heater comprising a heating portion; and
a sensing electrode, configured to comply with a shape of the heater, the sensing electrode comprising a sensing portion, wherein the heater and the sensing electrode are adjacent and arranged in parallel at different layers along a stacking direction, and the sensing electrode is electrically insulated from the heater;
wherein, on a reference plane in the stacking direction, a projection of the sensing portion of the sensing electrode is entirely covered by a projection of the heating portion of the heater.

2. The microelectromechanical sensor according to claim 1, wherein the heating portion of the heater is disposed to correspond with the thermal insulating cavity.

3. The microelectromechanical sensor according to claim 1, wherein the sensing portion of the sensing electrode comprises one or more interdigitated electrodes.

4. The microelectromechanical sensor according to claim 1, wherein the heater further comprises a heater arm connected with the heating portion, and the sensing electrode further comprises an electrode arm connected with the sensing portion.

5. The microelectromechanical sensor according to claim 4, wherein on the reference plane, a projection of the electrode arm is entirely covered by a projection of the heater arm.

6. The microelectromechanical sensor according to claim 1, wherein the heating portion of the heater comprises an outer frame section, a connecting section and a disc section, the outer frame section surrounds the connecting section and the disc section, and the disc section is connected with the outer frame section through the connecting section.

7. The microelectromechanical sensor according to claim 1, wherein the heating portion of the heater comprises a curved structure.

8. The microelectromechanical sensor according to claim 7, wherein the sensing portion of the sensing electrode comprises a pair of working electrodes extending along the curved structure and arranged in parallel.

9. The microelectromechanical sensor according to claim 1, further comprising an electrically insulating layer provided between the heater and the sensing electrode.

10. The microelectromechanical sensor according to claim 1, wherein the projection of the heating portion is larger than the projection of the sensing portion.

11. The microelectromechanical sensor according to claim 1, wherein a distance between an outermost edge of the heating portion and an outermost edge of the sensing portion is from 0.1 μm to 0.3 μm.

12. A sensing module for gas concentration monitoring, comprising:
a heater comprising a heating portion;
a sensing electrode, configured to comply with a shape of the heater, the sensing electrode comprising a sensing portion, wherein the heater and the sensing electrode are arranged in parallel at different layers along a stacking direction, and the sensing electrode is electrically insulated from the heater; and
a thermal insulating film under the sensing electrode along the stacking direction, wherein the thermal insulating film comprises a bump and a thermal insulating cavity, the bump protrudes upward from the thermal insulating film, such that the thermal insulating cavity is formed within a boundary defined by an inner profile of the bump;
wherein, on a reference plane in the stacking direction, a projection of the sensing portion of the sensing electrode is entirely covered by a projection of the heating portion of the heater.

13. The sensing module according to claim 12, wherein the sensing portion comprises one or more interdigitated electrodes.

14. The sensing module according to claim 12, wherein the heater further comprises a heater arm connected with the heating portion, and the sensing electrode further comprises an electrode arm connected with the sensing portion.

15. The sensing module according to claim 14, wherein on the reference plane, a projection of the electrode arm is entirely covered by a projection of the heater arm.

16. The sensing module according to claim 12, wherein the heating portion comprises an outer frame section, a connecting section and a disc section, the outer frame section surrounds the connecting section and the disc section, and the disc section is connected with the outer frame section through the connecting section.

17. The sensing module according to claim 12, wherein the heating portion comprises a curved structure.

18. The sensing module according to claim 17, wherein the sensing portion comprises a pair of working electrodes extending along the curved structure and arranged in parallel.

19. The sensing module according to claim 12, further comprising an electrically insulating layer provided between the heater and the sensing electrode.

\* \* \* \* \*